(12) United States Patent
Howe et al.

(10) Patent No.: US 6,589,326 B1
(45) Date of Patent: Jul. 8, 2003

(54) COATING FLUID FOR IMAGING ELEMENT COMPRISING SOLUBILIZED COLLAGEN GELATIN AND HARDENER

(75) Inventors: Andrew M. Howe, Watford (GB); Lloyd A. Lobo, Webster, NY (US); Gary L. Santee, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/158,681

(22) Filed: May 30, 2002

(51) Int. Cl.$^7$ .......................... G03C 1/047; G03C 1/30; C09H 3/00; C07K 1/00; C07K 14/00
(52) U.S. Cl. .................. 106/160.1; 430/621; 430/622; 430/642; 430/449; 530/354; 530/355
(58) Field of Search ................................ 430/642, 621, 430/622, 539, 466, 449, 537, 528; 106/160.1; 530/354, 355

(56) References Cited

U.S. PATENT DOCUMENTS

| | | | |
|---|---|---|---|
| 4,824,939 A | 4/1989 | Simpson | 530/355 |
| 5,236,822 A | 8/1993 | Riecke et al. | 430/623 |
| 5,731,134 A | 3/1998 | Honan et al. | 430/642 |
| 5,908,921 A | 6/1999 | LaRoche et al. | 530/354 |
| 5,919,906 A | 7/1999 | Rowlands et al. | 530/354 |
| 5,958,660 A | 9/1999 | Taylor et al. | 430/622 |
| 5,962,210 A | 10/1999 | Hahm et al. | 430/567 |
| 6,080,843 A | 6/2000 | Rainville et al. | 530/355 |
| 6,100,381 A | 8/2000 | Rowlands et al. | 530/355 |

FOREIGN PATENT DOCUMENTS

EP        0 971 262 A1        3/1989

OTHER PUBLICATIONS

Andrew M. Howe, Andrew Clarke, and Thomas H. Whitesides; "Viscosity Of Emulsions Of Polydisperse Droplets With A Thick Adsorbed Layer"; Langmuir; 1997; vol. 13; pp. 2617–2626.
Michael Dreja, Kurt Heine, Bernd Tieke and Gunter Junkers; "Effects Of Functionalized Latex Particles And Anionic Surfactants On The Flow Behavior Of Aqueous Gelatin Dispersions"; Journal Of Colloid And Interface Science; 1997; vol. 191; pp. 131–140.
K. Abraham Vaynberg, Norman J. Wagner, Ravi Sharma, and Peter Martic; "Structure And Extent Of Adsorbed Gelatin On Acrylic Latex And Polystyrene Colloidal Particles"; Journal Of Colloid And Interface Science; 1998; vol. 205; pp. 131–140.
K. Abraham Vaynberg and Norman J. Wagner; "Rheology Of Polyampholyte (Gelatin)–Stabilized Colloidal Dispersions: The Tertiary Electroviscous Effect"; Journal Rheology; 2001; vol. 45; pp. 451–466.
John H.E. Hone, Andrew M. Howe, and Thomas H. Whitesides; "Rheology Of Polystyrene Latexes With Adsorbed And Free Gelatin"; Colloids And Surfaces A: Physicochemical And Engineering Aspects; 2000; vol. 161; pp. 283–306.
US Patent Application No. 10/158,651; filed May 30, 2002; of Andrew M. Howe, Richard W. Connelly, James S. Honan, and Lloyd A. Lobo; titled "Coating Fluid For Imaging Element Comprising Solubilized Collagen Gelatin And Colloidal Dispersion".
US Patent Application No. 10/158,656; filed May 30, 2002; of Lloyd A. Lobo, Hwei–Ling Yau, James S. Honan and Paul T. Hahm; titled "Imaging Element Comprising Solubilized Collagen Gelatin And Hardener".

Primary Examiner—Richard L. Schilling
(74) Attorney, Agent, or Firm—Andrew J. Anderson

(57) ABSTRACT

An aqueous coating fluid is described comprising gelatin at a concentration of at least 1 wt % and gelatin hardener at a level from 1–200 effective μmole hardener per gram of coating fluid, wherein at least 20% of the gelatin comprises a gelatin prepared from hydrolysis of ossein using sodium or potassium hydroxide. Relative improvements are obtained in reducing the rate of chemical gelation of a coating fluid containing gelatin and a hardener, without the need for chemically modifying functional groups of the gelatin. The invention further enables an increase in coating fluid concentration, increase in the fluid viscosity, reduction in the ratio of added anionic polymer to gelatin, and/or increase in the pH of a coating fluid containing gelatin and a hardener, without detrimentally increasing the rate of chemical gelation of the coating fluid. The invention also enables the inclusion of relatively more reactive hardeners in a coating fluid containing gelatin, and/or the inclusion of relatively higher molecular weight gelatin in a coating fluid containing hardener, without detrimentally increasing the rate of chemical gelation of the coating fluid. Each such advantage may be achieved either individually, or in combinations to varying extents.

22 Claims, No Drawings

COATING FLUID FOR IMAGING ELEMENT COMPRISING SOLUBILIZED COLLAGEN GELATIN AND HARDENER

FIELD OF THE INVENTION

This invention relates to coating solutions comprising a hydrophilic colloid gelatin, which is prepared by the hydrolysis of ossein using sodium or potassium hydroxide, where the coating solution contains a gelatin hardener at a level of from 1–200 effective μmole hardener per gram of coating solution.

BACKGROUND OF THE INVENTION

Imaging elements, particularly photographic silver halide imaging elements, commonly use a hydrophilic colloid as a film forming binder for layers thereof, most commonly ossein. The layers of such imaging elements are typically coated employing multilayer slide bead coating processes such as described in U.S. Pat. No. 2,716,419 and multilayer slide curtain coating processes such as described in U.S. Pat. No. 3,508,947. The binder of choice in most cases is gelatin, prepared from various sources of collagen (see, e.g., P. I. Rose, The Theory of Photographic Process, 4th Edition, edited by T. H. James (Macmillan Publishing Company, New York, 1977) p. 51–65). The binder is expected to provide several functions, primarily to provide an element with some level of mechanical integrity and contain all the materials within the imaging element, which are required to provide an image. In particular, in photographic elements, the binder is expected to facilitate the diffusion of materials into and out of the element during a wet processing step. Gelatin is particularly suitable to perform this function, since it can absorb water and swell during the processing steps. In addition, gelatin also forms a cross linked network below a critical setting temperature through non-covalent bonding, which prevents dissolution of the gelatin, when wet. However, most photoprocessing operations are carried out above the critical temperature, which would thereby melt the gelatin in a non-crosslinked form. In order to prevent the dissolution of the gelatin during the photoprocessing operation, the gelatin is crosslinked chemically, with a hardener, during the manufacture of the imaging element.

Performance of the binder system may also be altered via chemical modification of the gelatin employed, as well as the choice and level of the hardener. Most of the hardeners used in practice act by reacting moieties on the hardener with the free amine groups on the gelatin. Lysine and hydroxylysine are the two predominant amino acids in gelatin that contribute the primary amine groups. Chemical modification of gelatin by increasing the amount of free amine groups have been disclosed in U.S. Pat. Nos. 5,316,902, 5,439,791 and EP 614930 and EP 813,109. These patents disclose elements wherein the carboxylic acid containing amino acids are reacted with moieties that can further react with vinyl sulfonyl hardeners. These are directed towards providing differential hardening between layers of a multilayer coating. Modified gelatin has also been disclosed in U.S. Pat. No. 4,590,151 for use in a top layer of a multilayer coating to reduce the amount of reticulation during photoprocessing. While chemical modification of gelatin may increase the wet mechanical properties of the imaging element, it is not easy or inexpensive to carry out. It adds an extra step in the gelatin manufacturing process and includes additional cost of the reactants needed. Other methods of improving the wet mechanical properties are by including other polymers along with gelatin. These polymers may be in the form of latexes as disclosed in U.S. Pat. No. 4,495,273 or as gelatin substitutes as disclosed in U.S. Pat. No. 4,019,908. Other attempts to improve the mechanical properties of the element, in the wet state, are related to improving the adhesion of the gelatin element to the substrate on which it is coated. EP 727698 discloses the use of specific solvents in layer adjacent to the support. However, even if the adhesion problems are solved, the cohesive strength or the wet strength property still may need to be improved.

Optimization of chemical hardening properties of a coated layer comprising gelatin is critical. While some attempts to optimize performance of the binder system have been carried out via chemical modification of the gelatin employed as discussed above, most attempts to optimize the binder system have focused on the choice and level of the hardener. It is the chemical hardening that renders the coating insoluble, and provides the required durability. The amount of hardener used, relative to the amount of gelatin present, is typically primarily a compromise of the swell of the wet element, the mechanical integrity, and cost. If too much hardener is used, the imaging element will not swell much, thereby, reducing the mobility of the various species required to permeate the element during processing. If too little hardener is used, however, when the element is in the developing solution, and immediately after removal from the developing solutions, it may be easily scratched while wet as the amount of chemical crosslinking is less and the coating becomes mushy, and prone to damage if it comes into contact with the hardware of the photoprocessor. Such scratches to the surface of the element may cause an unacceptable image to be formed. The third factor is cost of the hardener. It is always desirable to be able to use less hardener.

Gelatin hardener is typically introduced into one or more hydrophilic colloid layer compositions coated together in a coating pack. Usually, the hardener solution is mixed with a fluid that contains gelatin immediately prior to the coating hopper. This mixture is referred to as a coating fluid, and may also contain other photographically-useful materials. While hardener may be added individually to each hydrophilic colloid layer coating fluid, it is commonly added only to a limited number of such layers, commonly to only a single layer coating solution for a multilayer coating pack. After passing through the coating hopper, the hardener molecules diffuse into the various layers of the coating pack, cross-link the gelatin molecules and thus form a chemical gel that acts as a permanent network or matrix. Fast-acting hardeners are preferably used to increase the rate of cross-linking thereby allowing the aim physical properties, and often the associated aim sensitometric properties, to be met at shorter times. The most preferred fast acting hardeners are vinylsulfonyl hardeners, which react with the ∈-amino function of lysine and hydroxylysine. The primary benefit from use of such hardeners is more rapid release of product to customers, with a consequent reduction in inventory.

The reaction of hardener with gelatin commences immediately on mixing in the coating fluid and continues throughout the coating process. The residence time of the coating fluid in the hopper is often on the order of a minute, but may be considerably longer in any regions of re-circulating flow in or on the hopper, e.g. because of surface imperfections. Cross-linking of gelatin by hardener molecules therefore takes place in the period between mixing and final coating of the pack onto the web. The cross-linking can give rise to large aggregates and, potentially, chemical gelation. The formation of "gel slugs" (microgels) within the hopper may cause coating defects, specifically lines and streaks, which leads to waste of coated product. This is a particular issue with delivery of fast-acting (i.e. rapidly cross-linking) hardeners, as if a coating fluid gels rapidly, the tendency to form coating defects increases. The time taken to gel generally decreases when the concentration and viscosity of the coating fluid increase, and thus is particularly potentially problematic in hardener-bearing coating fluids wherein hardener for all the hydrophilic colloid layers is delivered through only a single or only a limited number of hydrophilic colloid layers coating fluids.

One of the most expensive processes in manufacturing of multilayer photographic products is drying of water after coating. If the concentration of solids within a coating fluid can be increased, then less water is coated and less drying is required at a given coating speed (or the coating speed can be increased without increasing the throughput capacity of the dryers). Furthermore, as the viscosity of the coating fluid is increased (preferably in excess of 5 mPa·s), the coating quality is improved as flow on the web after coating and ripple are reduced. To optimize the coating performance of the pack, the formulation of the coating fluid containing hardener also desirably should have a viscosity close to that of the adjacent layers in the coating pack. As a consequence of the increase in rate of gelation with increasing viscosity and the problems caused by gel slugs, however, coating fluids containing hardener often are required to be formulated with a lower viscosity than the fluids in adjacent layers, and with a higher dilution than desirable. This reduces coating quality and increases the load on the dryer. Therefore hardener-bearing coating fluids which can be formulated with a relatively higher viscosity and with a sufficiently long gelation time would be advantaged.

Polyanion thickeners may be included in hardener-bearing coating fluids to increase the viscosity without increasing significantly the gelation time. However, high levels of polyanion can be detrimental to the wet physical strength of the coating and can impact the sensitometry. An example of an effective polyanion thickener is a polymer of sodium 2-acrylamido-2-methylpropane sulfonate, which is even more effective when co-polymerised with acrylamide. Reducing the pH of the coating fluid can also reduce the rate of reaction of vinylsulfonyl hardeners with gelatin. However, as the pH is reduced towards and below the gelatin isoelectric pH, coating fluids containing polyanionic thickeners become unstable to coacervation. Furthermore, the practical range of pH for the coating fluid may be limited by sensitometric affects, such as raw-stock keeping.

High purity gelatins are generally required for imaging applications. Currently the most commonly employed manufacturing process for obtaining high purity gelatins involves demineralization of a collagen containing material, typically cattle bone (ossein), followed by extended alkaline treatment (liming) and finally gelatin extractions with water of increasing temperature as described in U.S. Pat. Nos. 3,514,518 and 4,824,939. The gelatin produced by this process, commonly referred to as lime processed ossein gelatin, has existed with various modifications throughout the gelatin industry for a number of years. The liming step of this process requires up to 60 days or more, the longest step in the approximately 3 month process of producing gelatin. The hydrolyzed collagen is extracted in a series of steps to obtain several gelatin fractions with varying molecular weights. In order to obtain gelatin of desired molecular weight to provide suitable coating solution viscosities, these fractions can be further hydrolyzed by high temperature hydrolysis. The fractions are then blended to obtain the appropriate molecular weight for photographic use. U.S. Pat. No. 5,908,921 describes a relatively new process for the preparation of photographic grade gelatin, where the agent for hydrolysis is a strong alkali, such as sodium or potassium hydroxide. The reaction rate is disclosed to be from 10 to 120 hours (substantially faster than the prior lime processes), after which a single extraction step yields a single batch of gelatin, which is then purified and deionized. The characteristics of the gelatin produced are that it has a high gel strength and narrow molecular weight distribution compared to gelatins produced by the conventional process where lime is used as the agent for hydrolysis. There is no disclosure in U.S. Pat. No. 5,908,921, however, regarding any possible impact that use of the gelatin produced by such process may have on aqueous coating fluids containing such gelatin and a gelatin hardener.

SUMMARY OF THE INVENTION

In accordance with the invention, an aqueous coating fluid is described comprising gelatin at a concentration of at least 1 wt % and gelatin hardener at a level from 1–200 effective μmole hardener per gram of coating fluid, wherein at least 20% of the gelatin comprises a gelatin prepared from hydrolysis of ossein using sodium or potassium hydroxide.

The present invention enables relative improvements in reducing the rate of chemical gelation of a coating fluid containing gelatin and a hardener, without the need for chemically modifying functional groups of the gelatin. The invention further enables an increase in coating fluid concentration, increase in the fluid viscosity, reduction in the ratio of added anionic polymer to gelatin, and/or increase in the pH of a coating fluid containing gelatin and a hardener, without detrimentally increasing the rate of chemical gelation of the coating fluid. The invention also enables the inclusion of relatively more reactive hardeners in a coating fluid containing gelatin, and/or the inclusion of relatively higher molecular weight gelatin in a coating fluid containing hardener, without detrimentally increasing the rate of chemical gelation of the coating fluid. Each such advantage may be achieved either individually, or in combinations to varying extents.

DETAILED DESCRIPTION OF THE INVENTION

High purity gelatins are required for imaging/photographic applications. One gelatin property of interest is absorbance at 420 nm (A420), commonly know as color. The lower the A420 of gelatin the clearer the gelatin layer is in coated products. The A420 of gelatin is one of the defining factors for determining applicability of the gelatin for imaging applications. Edible gelatins are typically higher than photographic gelatins in A420. Two other gelatin properties critical to imaging applications are viscosity and gel strength or Bloom. Ideally, use of a gelatin with relatively high gel strength and low viscosity would be advantageous to coated products. High gel strength is desired for gelatin setting properties. Reducing gelatin viscosity allows coating fluids to be concentrated without increasing their viscosity, thereby reducing dryer loading and enabling higher coating speeds. Due to variable bond breakage during manufacture, gelatin is composed of a distribution of polypeptides of varying molecular weights. Aqueous size exclusion chromotography provides a method of analysis for determining the gelatin molecular weight distribution. This distribution is described as containing the following fractions; high molecular weight or HMW (>250 kD); Beta (250–150 kD); Alpha (150–50 kD); Subalpha (50–20 kD); and low molecular weight or LMW (20–4 kD). In general, high gel strength correlates with high gelatin alpha fraction content, and high viscosity correlates with high gelatin HMW fraction content. The viscosity of a gelatin solution at a specified concentration is itself often used to characterize the mean molecular weight of a particular gelatin sample. Typical alkaline processed bone gelatins contain relatively high gel strength and high viscosity. Gelatin viscosity can be controlled during the gelatin manufacturing process with heat treatment. Heat treatment, however, reduces both gel strength and viscosity. Typical gel strengths are from 250 to 300 Bloom and typical viscosities are from 5 to 15 cP (for a 6.16 wt % gelatin solution, measured at 40 C).

At least 20% of the gelatin of an aqueous coating fluid comprising gelatin and a gelatin hardener in accordance with the invention comprises a gelatin prepared from a process comprising hydrolysis of ossein utilizing a caustic sodium or potassium hydroxide solution to produce gelatin from a collagen containing material, such as described in U.S. Pat. No. 5,908,921, the disclosure of which is incorporated by reference herein. The process for the manufacture of gelatin as taught in U.S. Pat. No. 5,908,921 includes providing a collagen containing material and demineralizing the collagen containing material to produce ossein which is homogenized or ground. The ossein is added to a water solution of sodium hydroxide or potassium hydroxide at a concentration of at least 4% by weight and a swelling restraining salt (ie. sodium sulfate) at a concentration of at least 3% by weight for a time sufficient (typically 10 to 120 hours) to form a reacted slurry. The slurry is heated at a temperature of at least 45 C. for a time sufficient (typically at least 30 minutes) to produce a gelatin containing solution. The gelatin containing solution is clarified by raising the pH of the solution to greater than 9.8. A sulfate salt of a divalent or trivalent metal is added to the gelatin solution to reduce the pH to between 7.0 and 8.0. An acid, preferably phosphoric, is added to the solution to reduce the pH to between 5.0 and 6.0. A polymeric flocculant is added to the gelatin containing solution at a weight percent of 0.1 based on the dry weight of the gelatin to form a floc which is removed. Following extraction and clarification the gelatin solution is filtered, oxidized or deionized to achieve desired levels of microconstituents, prior to concentration and drying. The rate of reaction with the collagen is a function of caustic concentration, salt concentration, temperature and time. The process is further specifically illustrated by Example 1 of U.S. Pat. No. 5,908,921.

Typical collagen containing materials include skins, bones and hides (i.e., any connective tissue of an animal body). Sources of animal bodies include cattle, pigs and sheep. Cattle bone is preferred, although other sources of bone can be effectively utilized in the present invention. A continuous process for leaching cattle bone is described in U.S. Pat. No. 4,824,939, incorporated herein by reference. In this process the bovine bone is placed into contact with an acid, typically hydrochloric acid. The acid reacts with the minerals contained in the bone to form soluble products, such as calcium chloride and phosphoric acid. These products are leached out of the bone and removed, typically as calcium hydrogen phosphate dihydrate. The demineralized bone or ossein is one source of collagen from which gelatin can be extracted.

A gelatin prepared by hydrolysis of ossein using sodium or potassium hydroxide as described above and which is employed in the coating fluids of the invention is hereafter referred to as a "solubilized collagen" gelatin, as collagen from the source material is completely solubilized. Gelatin obtained therefrom is dissolved in a single extraction, and the described process advantageously creates a very uniform gelatin with minimal time and energy. The extracted gelatin may be purified through the use of a clarification process and desalted, typically using ultrafiltration or electrodialysis technology. Although the molecular weight of the gelatin obtained may be relatively high (such as obtained in U.S. Pat. No. 5,908,921 Example 1), the proteolytic degradation of gelatin (such as disclosed, e.g., in U.S. Pat. Nos. 5,919, 906, 6,080,843, and 6,100,381) can be advantageously used to reduce the molecular weight to a desired range. The characteristics of the gelatin produced, using these methods is that it has a relatively high gel strength and narrow molecular weight distribution compared to gelatins produced by the conventional process where lime is used as the agent for hydrolysis. It has been surprisingly found that use of solubilized collagen gelatin with such relatively narrow molecular weight distribution in aqueous coating fluids with a chemical crosslinker in accordance with the invention enables relative improvements in reducing the rate of chemical gelation of the coating fluid, without the need for chemically modifying functional groups of the gelatin.

There are several classes of chemical crosslinkers/ hardeners that can be used for gelatin. These are described in, e.g., "The Theory of the Photographic Process" $4^{th}$ Ed., Ed. T. H. James, pg. 77–87, 1977. Hardeners can be either inorganic or organic in nature, and may be polymeric or non-polymeric. Typical inorganic hardening agents comprise multivalent cations, including salts of chromium and some salts of aluminum. These hardeners typically crosslink via the free carboxylic acids in gelatin and the degree of crosslinking is pH sensitive and also reversible. It is not preferable, however, to use these materials for absorbents because of the impact these materials have on the environment. The organic hardeners act via the ∈-amino function of lysine and hydroxylysine. There are on the average of 350–400 $\mu$mole of lysine and about 20% of that amount of hydroxylysine per gram of dry gelatin. Classes of organic hardeners include, but are not limited to, aldehydes and blocked aldehydes, ketones, carboxylic and carbamic acid derivatives, active olefins, s-triazines, epoxides, aziridines, isocyanates, carbodiimides and isoxazolium salts, pyridinium ethers, carbamoyl- and carbamoyloxy-pyridinium ions, and sulfone based hardeners such as sulfonate esters and sulfonyl halides. Polymeric hardeners are generic polymer molecules bearing one or more of the above moieties in their chain.

In particular, the use of vinyl sulfone hardeners such as 1,2-bis(vinyl-sulfonyl)methane, 1,2- bis(vinyl-sulfonyl) methane ether, and 1,2-bis(vinyl-sulfonyl acetoamido) ethane, and other hardeners such as 2,4-dichloro-6-hydroxy-s-triazine, triacryloyl-triazine, and pyridinium, 1-(4-morpholinylcarbonyl)-4-(2-sulfoethyl)-, inner salt are particularly useful. Also useful are so-called fast acting hardeners as disclosed in U.S. Pat. Nos. 4,418,142; 4,618, 573; 4,673,632; 4,863,841; 4,877,724; 5,009,990; 5,236, 822. The selection of the hardener type most useful for a particular application depends on the efficacy of the crosslinking, its toxicity in the native state and the residuals in the absorbent, and cost.

In preferred embodiments of the invention, the hardener is a vinyl-sulfone hardener. Vinyl-sulfone hardeners are well known. Typical vinyl-sulfone hardeners are described in U.S. Pat. Nos. 3,490,911, 3,539,644, 3,642,486, 3,841,872, 4,670,377, 4,897,344, 4,975,360 and 5,071,736, the entire disclosures of which are incorporated herein by reference. Preferred vinyl-sulfone hardeners for use in the present invention are represented by Formula (C) indicated below:

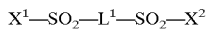  (C)

wherein $X^1$ and $X^2$ represent —CH=CH$_2$ or —CH$_2$CH$_2$—Y$^1$ groups, and $X^1$ and $X^2$ may be the same or different; $Y^1$ represents a group which can be substituted by a nucleophilic reagent having a nucleophilic group, or a group which can be eliminated in the form of HY$^1$ by means of a base; and $L^1$ is a divalent linking group which may be substituted.

Preferred examples of the groups $X^1$ and $X^2$ are indicated below:
—CH=CH$_2$, —CH$_2$CH$_2$—Cl, —CH$_2$CH$_2$—Br, —CH$_2$CH$_2$—OSO$_2$CH$_3$, —CH$_2$CH$_2$—OSO$_2$C$_6$H$_5$, —CH$_2$CH$_2$—OSO$_2$C$_6$H$_4$—CH$_3$, —CH$_2$CH$_2$—OSO$_3$Na, —CH$_2$CH$_2$—OSO$_3$K, —CH$_2$CH$_2$—OCOCH$_3$, —CH$_2$CH$_2$—OCOCF$_3$, —CH$_2$CH$_2$—OCOCHCl$_2$, —CH$_2$CH$_2$—N$^+$—C$_6$H$_5$(Cl$^-$), —CH$_2$CH$_2$—N$^+$—C$_6$H$_4$-p-CH$_2$CH$_2$SO$_3^-$, —CH$_2$CH$_2$—N$^+$—C$_6$H$_4$-m-NHCH$_2$SO$_3^-$ The group —CH=CH$_2$ is the most desirable for $X^1$ and $X^2$.

The divalent linking group $L^1$ is a divalent group preferably having up to 30 carbon atoms, more preferably up to 10 carbon atoms, and comprising an alkylene group (including cycloalkylene groups), an arylene group (including heterocyclic aromatic groups such as 5- to 7-membered ring groups containing 1 to 3 hetero atoms (e.g., a divalent group derived from thiadiazole or pyridine)) or combinations of these groups with one or more units represented by —O—, —NR$^2$—, —SO.sub.2-, —SO. sub.3-, —S—, —SO—, —SO$_2$NR$^2$—, —CO—, —COO—, —CONR$^2$—, —NR$^2$COO— and —NR$^2$CONR$^2$—, where R$^2$ represents hydrogen or an alkyl group having from 1 to 15 carbon atoms, an aryl group or an aralkyl group. The R$^2$ groups may be joined together to form ring structures when the linking group includes two or more units of —NR$^2$—, —SO$_2$NR$^2$—, —CONR$^2$—, —NR$^2$COO— and —NR$^2$CONR$^2$—. Moreover, $L^1$ may also be substituted by, for example, hydroxyl groups, alkoxy groups, carbamoyl groups, sulfamoyl group, sulfo groups or salts thereof, carboxyl groups or salts thereof, halogen atoms, alkyl groups, aralkyl groups and aryl groups. Furthermore, the substituent groups may be further substituted with one or more groups represented by $X^3$—SO$_2$—, where $X^3$ has the same significance as $X^1$ and $X^2$ described above.

The groups indicated below are typical examples of the linking group $L^1$. In these examples, a–k are integers of from 1 to 6. Of these, e can also have a value of zero, but e is preferably 2 or 3. The values of a–k except e are preferably 1 or 2, and most desirably are 1. In these formulae, R$^2$ preferably represents a hydrogen atom, or an alkyl group having from 1 to 6 carbon atoms, and most desirably represents a hydrogen atom, a methyl group or an ethyl group. $L^1$ is preferably: —(CH$_2$)$_a$—, —(CH$_2$)$_b$—O—(CH$_2$)$_c$—, —(CH$_2$)$_d$—CONR$^2$—(CH$_2$)$_e$—NR$^2$CO—(CH$_2$)$_f$—, —(CH$_2$)$_g$—SO$_2$—(CH$_2$)$_h$—,

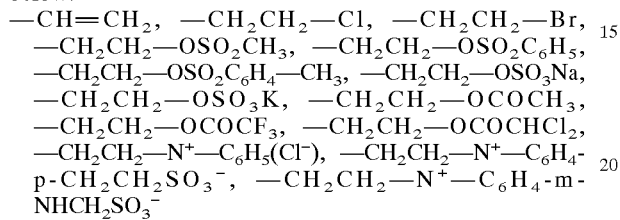

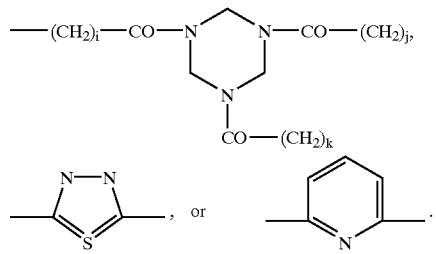

Typical nonlimiting examples of the film hardening agents for use in the present invention are indicated below.

H-1: CH$_2$=CHSO$_2$CH$_2$SO$_2$CH=CH$_2$
H-2: CH$_2$=CHSO$_2$CH$_2$OCH$_2$SO$_2$CH=CH$_2$
H-3: CH$_2$=CHSO$_2$CH$_2$CH$_2$CH$_2$SO$_2$CH=CH$_2$
H-4: CH$_2$=CHSO$_2$CH$_2$CH(OH)CH$_2$SO$_2$CH=CH$_2$
H-5: CH$_2$=CHSO$_2$CH$_2$CONHCH$_2$CH$_2$NHCOCH$_2$SO$_2$CH=CH$_2$
H-6: CH$_2$=CHSO$_2$CH$_2$CONHCH$_2$CH$_2$CH$_2$NHCOCH$_2$SO$_2$CH=CH$_2$

H-7:

H-8:
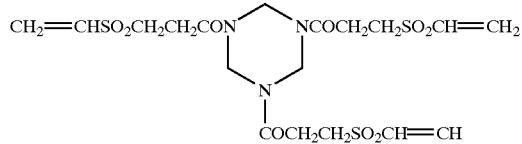

H-9:
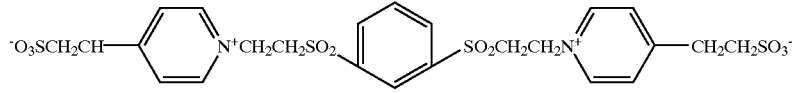

H-10:
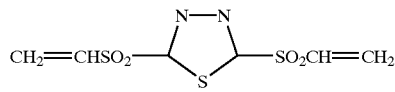

H-11: $(CH_2=CHSO_2CH_2)_3CCH_2SO_2CH_2CH_2NHCH_2CH_2SO_3Na$

H-12: $(CH_2=CHSO_2)_2CHCH_2CH_2—C_6H_4—SO_3Na$

In one embodiment of the invention, the hardener is preferably a non-polymeric bis(vinyl-sulfone), such as bis(vinyl-sulfonyl)methane (BVSM), bis(vinyl-sulfonyl methyl)ether (BVSME), or 1,2-bis(vinyl-sulfonyl acetoamide)ethane (BVSAE), etc. Non-polymeric vinyl-sulfone hardeners preferably have a molecular weight of less than 10,000, and more preferably of about 100 to about 5,000.

In other embodiments of the invention, a polymeric vinyl-sulfone hardener may be used, such as the polymeric hardeners disclosed in U.S. Pat. Nos. 4,161,407, 4,460,680 and 4,481,284, the entire disclosures of which are incorporated herein by reference. Preferred polymeric vinyl-sulfone hardeners are represented by Formula (D):

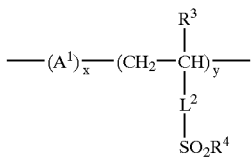

wherein $A^1$ is a monomer unit prepared by copolymerizing copolymerizable ethylenically unsaturated monomers, $R^3$ is hydrogen or a lower alkyl group having 1 to 6 carbon atoms; $L^2$ is a bivalent linking group, and $R^4$ is —CH=CH$_2$ or —CH$_2$CH$_2$X$^4$, where X$^4$ is a group capable of being substituted with a nucleophilic group or a group capable of being released in the form of HX$^4$ upon addition of a base, and x and y each represents molar percent, x being between 0 and 99 and y being between 1 and 100.

Examples of ethylenically unsaturated monomer represented by $A^1$ of Formula (D) include ethylene, propylene, 1-butene, isobutene, styrene, chloromethylstyrene, hydroxymethylstyrene, sodium vinylbenzenesulfonate, sodium vinylbenzylsulfonate, N,N,N-trimethyl-N-vinylbenzylammonium chloride, N,N-dimethyl-N-benzyl-N-vinylbenzylammonium chloride, a-methylstyrene, vinyltoluene, 4-vinylpyridine, 2-vinylpyridine, benzyl vinylpyridinium chloride, N-vinylacetamide, N-vinylpyrrolidone, 1-vinyl-2-methylimidazole, monoethylenically unsaturated esters of aliphatic acids (e.g., vinyl acetate and allyl acetate), ethylenically unsaturated mono- or dicarboxylic acids and salts thereof (e.g., acrylic acid, methacrylic acid, itaconic acid, maleic acid, sodium acrylate, potassium acrylate and sodium methacrylate), maleic anhydride, esters of ethylenically unsaturated monocarboxylic or dicarboxylic acids (e.g., n-butyl acrylate, n-hexyl acrylate, hydroxyethyl acrylate, cyanoethyl acrylate, N,N-diethylaminoethyl acrylate, methyl methacrylate, n-butyl methacrylate, benzyl methacrylate, hydroxyethyl methacrylate, chloroethyl methacrylate, methoxyethyl methacrylate, N,N-diethylaminoethyl methacrylate, N,N,N-triethyl-N-methacryloyloxyethylammonium-p-toluene sulfonate, N,N diethyl-N-methyl-N-methacryloyloxy-ethyl ammonium-p-toluene sulfonate, dimethyl itaconate and monobenzyl maleate), and amides of ethylenically unsaturated monocarboxylic or dicarboxylic acids (e.g., acrylamide, N,N-dimethylacrylamide, N-methylolacrylamide, N-(N,N-dimethylaminopropyl)acrylamide, N,N,N-trimethyl-N-(N-acryloylpropyl)ammonium-p-toluene sulfonate, sodium 2-acrylamide-2-methylpropane sulfonate, acryloyl morpholine, methacrylamide, N,N-dimethyl-N'-acryloyl propane diamine propionate betaine, and N,N-dimethyl-N'-methacryloyl propane diamine acetate betaine). $A^1$ further includes monomers having at least two copolymerizable ethylenically unsaturated groups (e.g., divinylbenzene, methylenebisacrylamide, ethylene glycol diacrylate, triethylene glycol diacrylate, ethylene glycol dimethacrylate, trimethylene glycol dimethacrylate and neopentyl glycol dimethacrylate).

Examples of $R^3$ of Formula (D) include methyl, ethyl, butyl, tert-butyl, isopropyl, n-hexyl and the like.

Examples of $R^4$ of Formula (D) include the following groups: —CH=CH$_2$, —CH$_2$CH$_2$Cl, —CH$_2$CH$_2$Br, —CH$_2$CH$_2$O$_3$SCH$_3$, —CH$_2$CH$_2$OH, —CH$_2$CH$_2$O$_2$CCH$_3$, —CH$_2$CH$_2$O$_2$CCF$_3$, —CH$_2$CH$_2$CH, —CH$_2$CH$_2$O$_2$CCH$_3$, and —CH$_2$CH$_2$O$_2$CCHCl$_2$.

$L^2$ of formula (D) is a bivalent linking group. In one preferred embodiment, $L^2$ is an alkylene group, preferably containing about 1 to 6 carbon atoms, an arylene group, preferably containing about 6 to 12 carbon atoms, —COZ—, or —COZR$^5$— where R$^5$ is an alkylene group, preferably containing about 1 to 6 carbon atoms, or an arylene group, preferably containing about 6 to 12 carbon atoms. Preferably $L^2$ is a phenylene group.

In another embodiment of the invention $L^2$ is preferably a linking group of the formula —Q—L$^3$—, wherein Q is —CO$_2$— or —C(R$^6$)ON—, wherein R$^6$is hydrogen, a lower alkyl group having 1–6 carbon atoms or an arylene group having 6 to 10 carbon atoms; L$^3$ is a divalent group having 3 to 15 carbon atoms and containing at least one linking group selected from the members consisting of —CO$_2$— and —C(R$^7$)ON— wherein R$^7$ is the same as R$^6$ above or a divalent group having 1 to 12 carbon atoms and containing at least one linking group selected from the members consisting of —O—, —N(R$^8$)—, —CO—, —SO—, —SO$_2$—, —SO$_3$—, —SO$_2$N(R$^8$)—, —N(R$^8$)CON(R$^8$)—, and —N(R$^8$)CO$_2$—, wherein R$^8$ is hydrogen or a lower alkyl group having 1–6 carbon atoms.

The molecular weight of polymeric hardeners is generally greater than 10,000, typically in the range of 10,000 to 1,000,000, and more typically 30,000 to 500,000.

Other hardeners which may be used in this invention include carbamoyl- and carbamoyloxy-pyridinium hardeners which are disclosed, for example, in U.S. Pat. Nos. 4,063,952, 4,119,464, 4,828,974 and 4,751,173, and Japanese Kokai No. 61/009,641, and pyridinium hardeners which are disclosed, for example, in U.S. Pat. Nos. 5,263, 822 and 4,877,724, the entire disclosures of which are incorporated herein by reference.

In accordance with the invention, for coating fluids comprising gelatin and gelatin hardener which have similar concentrations and viscosities, it has surprisingly been found that gelation times are significantly extended when a solubilized collagen gelatin is employed rather than a conventional lime processed gelatin. The advantages of the invention are particularly applicable to hardener-bearing coating fluids which are intended to supply sufficient amount of hardener for multiple hydrophilic colloid layers in addition to the hardener-bearing layer itself (e.g., where the hardener-bearing layer coating fluid is coated in combination with an additional hydrophilic colloid layer coating fluid which does not contain hardener). A useful concentration range of crosslinker for such hardener-bearing coating fluids is typically from 1–200 effective $\mu$mole (i.e., $1\times10^{-6}$ to $2\times10^{-4}$ effective mole) hardener per gram of coating fluid, preferably 10–100, more preferably 10–70, and most preferably 20–60 effective $\mu$mole/g of coating fluid. For purposes of this invention we define an "effective mole" of hardener as the number of hardener compound molecules required to provide reaction sites for two moles of reactive moieties of gelatin. Thus, for a simple difunctional organic hardener compound like formaldehyde an effective mole is equal to an actual mole of hardener compound. For a trifunctional hardener compound, an effective mole would comprise ⅔ of an actual mole of trifunctional hardener, whereas for a polymeric hardener the effective moles is calculated based on the average number of monomer units of the polymeric compound that provide the species groups which act as crosslinkers. Thus for the preferred concentration ranges of hardener given above, the number of effective moles of crosslinking species should be considered.

In a particular embodiment of the invention, hardener-bearing coating fluids comprising a solubilized collagen gelatin which has a η20% solution viscosity of greater than 30 mPa·s, more preferably greater than 40 mPa·s, where the η20% solution viscosity is that of a 20 wt % gelatin solution, measured at 45 C., may advantageously be formulated without generating undesirable short gelation times which may otherwise be observed with use of solely conventional lime-processed gelatins of similar solution viscosities in such coating fluids. The invention further facilitates preparation of hardener-bearing coating fluids having a low-shear viscosity of the fluid above 3 mPa·s when measured at 45° C., more preferably above 5 mPa·s when measured at 45° C.

While aqueous coatings fluids in accordance with the invention comprise at least 1 wt % gelatin, the advantages provided by the invention are particularly applicable to higher concentration coating fluids, such as coating fluids comprising 3 wt % gelatin or more, preferably 4 wt % gelatin or more, and especially 5 wt % gelatin or more, which contain gelatin hardener. Further, the invention is particularly applicable to coating fluids wherein gelatin hardener is present at a level greater than 100 effective lmole hardener per gram of gelatin in solution, more particularly greater than 300 effective mol and even more particularly greater than 500 effective mole hardener per gram of gelatin in solution, such as for hardener-bearing coating fluids which are intended to supply sufficient amount of hardener for multiple hydrophilic colloid layers as discussed above, where gelation and pre-mature crosslinking potentially become more problematic. The advantages of the invention are applicable to coating fluids prepared for multilayer slide bead coating processes such as described in U.S. Pat. No. 2,716,419 as well as multilayer slide curtain coating processes such as described in U.S. Pat. No. 3,508,947.

Although, it may be desirable from a cost and performance standpoint to replace all the gelatin in hydrophilic colloid layer coating fluids for imaging elements with solubilized collagen gelatin, even partial replacement of the gelatin in a hardener-bearing layer coating fluid provides a manufacturing improvement proportional to the fraction of solubilized collagen gelatin present. Thus, while the present invention is broadly directed towards the use of solubilized collagen gelatin in an amount of at least 20% of the gelatin in a hardener-bearing layer coating fluid, it is preferable to have at least 30% as the solubilized collagen gelatin and more preferable to have at least 50% of solubilized collagen gelatin as the gelatin in the hardener-bearing coating fluids of the invention. The hardener-bearing aqueous gelatin coating fluids may further comprise additional components typically used in imaging elements, such as dispersions of photographically useful compounds, and anionic polymeric thickeners. In a specific embodiment of the invention, e.g., the coating fluid may advantageously comprise an anionic polymeric thickener at a concentration above 0.01% wt %.

In addition to providing coating fluid manufacturing advantages, the use of solubilized collagen gelatin in combination with certain effective amounts of gelatin hardener in imaging elements has been found to enable relative improvements in the wet mechanical strength of an imaging element comprising gelatin as a binder, without needing to increase the amount of chemical crosslinker with respect to the gelatin. Imaging elements comprising a specified level of solubilized collagen gelatin in one or more hydrophilic colloid layer thereof in combination with a specified effective level of gelatin hardener per gram of gelatin are described in commonly assigned, concurrently-filed, co-pending application U.S. Ser. No. 10/158,656, the disclosure of which is incorporated herein by reference. The hardener in such imaging elements may be delivered through the coating fluid comprising the solubilized collagen gelatin, or a separate hardener-bearing layer coated therewith.

Coating fluids comprising gelatin and a hardener in accordance with the invention may additionally comprise a colloidal dispersed material phase. A further advantage to the use of solubilized collagen gelatin is that such gelatin enables increasing the concentrations of a coating fluid containing gelatin and dispersed sub-micron colloidal materials, reducing the size of the sub-micron colloidal materials in such a coating fluid, and/or including higher molecular weight gelatin in such a coating fluid without detrimentally increasing the viscosity of such fluids. Alternatively the use of a solubilized collagen gelatin enables reducing the viscosity of an aqueous coating fluid containing gelatin and dispersed insoluble colloidal material, without needing to reduce the concentration of gelatin or colloidal materials, increase the size of the sub-micron colloidal materials, and/or reduce the molecular weight of the gelatin. Coating fluids containing specified levels of solubilized collagen gelatin and a colloidal dispersed material phase are described in commonly assigned, concurrently-filed, co-pending application U.S. Ser. No. 10/158,651, the disclosure of which is incorporated herein by reference.

Hardener-bearing coating fluids of the invention may be employed in the manufacture of many different types of imaging elements, depending on the particular use for which they are intended. Details with respect to the composition and function of a wide variety of different imaging elements are provided in U.S. Pat. No. 5,300,676 and references described therein. Such elements include, for example, photographic, electrophotographic, electrostatographic, photothermographic, migration, electrothermographic, dielectric recording and thermal-dye-transfer imaging elements. Layers of imaging elements other than the image-forming layer are commonly referred to auxiliary layers. There are many different types of auxiliary layers such as, for example, subbing layers, backing layers, interlayers, overcoat layers, receiving layers, stripping layers, antistatic layers, transparent magnetic layers, and the like.

The hardener-bearing coating fluids of this invention in particular may be used in the manufacture of photographic elements, such as photographic films, photographic papers or photographic glass plates, in which the image-forming layer is a radiation-sensitive silver halide emulsion layer. The thickness of the support is not critical. Film support thickness of 2 to 10 mil (0.05 to 0.25 millimeters), and thicker paper supports, e.g., typically can be used. The supports typically employ an undercoat or subbing layer well known in the art that comprises, for example, for polyester support a vinylidene chloride/methyl acrylate/itaconic acid terpolymer or vinylidene chloride/acrylonitrile/acrylic acid terpolymer. The emulsion layers typically comprise a film-forming hydrophilic colloid. The most commonly used of these is gelatin and a solubilized collagen gelatin as described above is a particularly preferred material for use in photographic emulsion layers in such embodiments.

Photographic imaging elements can be black and white, single color or multicolor photographic elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer. Depending upon the dye-image-providing material employed in the photographic element, it can be incorporated in the silver halide emulsion layer or in a separate layer associated with the emulsion layer. The dye-image-providing material can be any of a number known in the art, such as dye-forming couplers, bleachable dyes, dye developers and redox dye-releasers, and the particular one employed will depend on the nature of the element, and the type of image desired. Dye-image-providing materials employed with conventional color photographic materials designed for processing with a separate developing solution are preferably dye-forming couplers; i.e., compounds which couple with oxidized developing agent to form a dye. Preferred couplers which form cyan dye images are phenols and naphthols. Preferred couplers which form magenta dye images are pyrazolones and pyrazolotriazoles. Preferred couplers which form yellow dye images are benzoylacetanilides and pivalylacetanilides.

A typical multicolor photographic element comprises a support bearing a cyan dye image-forming unit comprised of at least one red- sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like. All of these can be coated on a support which can be transparent or reflective (for example, a paper support). Photographic elements may also usefully include a magnetic recording material as described in Research Disclosure, Item 34390, November 1992, or a transparent magnetic recording layer such as a layer containing magnetic particles on the underside of a transparent support as in U.S. Pat. Nos. 4,279,945 and 4,302,523. The element typically will have a total thickness (excluding the support) of from 5 to 30 microns. While the order of the color sensitive layers can be varied, they will normally be red-sensitive, green-sensitive and blue-sensitive, in that order on a transparent support, (that is, blue sensitive furthest from the support) and the reverse order on a reflective support being typical. The present invention also contemplates the use of photographic imaging elements in accordance with of the present invention in what are often referred to as single use cameras (or "film with lens" units). These cameras are sold with film preloaded in them and the entire camera is returned to a processor with the exposed film remaining inside the camera. Such cameras may have glass or plastic lenses through which the photographic element is exposed.

In the following discussion of suitable materials for use in imaging elements, reference will be made to Research Disclosure, September 1994, Number 365, Item 36544, which will be identified hereafter by the term "Research Disclosure I." The Sections hereafter referred to are Sections of the Research Disclosure I unless otherwise indicated. All Research Disclosures referenced are published by Kenneth Mason Publications, Ltd., Dudley Annex, 12a North Street, Emsworth, Hampshire P101 7DQ, ENGLAND. The foregoing references and all other references cited in this application, are incorporated herein by reference.

Silver halide emulsions which may be employed in photographic imaging elements may be negative working, such as surface sensitive emulsions or unfogged internal latent image forming emulsions, or positive working emulsions of internal latent image forming emulsions (that are either fogged in the element or fogged during processing). With negative working silver halide a negative image can be formed; optionally, a positive (or reversal) image can be formed although a negative image is typically first formed in the reversal process. Suitable emulsions and their preparation as well as methods of chemical and spectral sensitization are described in Sections I through V. Color materials and development modifiers are described in Sections V through XX. Vehicles (which can be used in combination with solubilized collagen gelatin in photographic imaging elements in accordance with the invention) are described in Section II, and various additives such as brighteners, antifoggants, stabilizers, light absorbing and scattering materials, hardeners, coating aids, plasticizers, lubricants and matting agents are described, for example, in Sections VI through XIII. Manufacturing methods are described in all of the sections, layer arrangements particularly in Section XI, exposure alternatives in Section XVI, and processing methods and agents in Sections XIX and XX.

Photographic imaging elements may also use colored couplers (e.g. to adjust levels of interlayer correction) and masking couplers such as those described in EP 213 490; Japanese Published Application 58-172,647; U.S. Pat. No. 2,983,608; German Application DE 2,706,117C; U.K. Patent 1,530,272; Japanese Application A-113935; U.S. Pat. No. 4,070,191 and German Application DE 2,643,965. The masking couplers may be shifted or blocked.

Photographic imaging elements may also contain materials that accelerate or otherwise modify the processing steps of bleaching or fixing to improve the quality of the image. Bleach accelerators described in EP 193 389; EP 301 477; U.S. Pat. Nos. 4,163,669; 4,865,956; and 4,923,784 are particularly useful. Also contemplated is the use of nucleating agents, development accelerators or their precursors (UK Patent 2,097,140; U.K. Patent 2,131,188); electron transfer agents (U.S. Pat. Nos. 4,859,578; 4,912,025); anti-fogging and anti color-mixing agents such as derivatives of hydroquinones, aminophenols, amines, gallic acid; catechol; ascorbic acid; hydrazides; sulfonamidophenols; and non color-forming couplers.

Imaging elements may also contain other filter dye layers comprising colloidal silver sol or yellow and/or magenta filter dyes and/or antihalation dyes (particularly in an undercoat beneath all light sensitive layers or in the side of the support opposite that on which all light sensitive layers are located) either as oil in water dispersions, latex dispersions or as solid particle dispersions. Additionally, they may be used with "smearing" couplers (e.g. as described in U.S. Pat. No. 4,366,237; EP 096 570; U.S. Pat. Nos. 4,420,556; and 4,543,323.) Also, the couplers may be blocked or coated in protected form as described, for example, in Japanese Application 61/258,249 or U.S. Pat. No. 5,019,492.

Photographic imaging elements may further contain other image-modifying compounds such as "Developer Inhibitor-Releasing" compounds (DIR's). Useful additional DIR's for elements of the present invention, are known in the art and examples are described in U.S. Pat. Nos. 3,137, 578; 3,148, 022; 3,148,062; 3,227,554; 3,384,657; 3,379,529; 3,615, 506; 3,617,291; 3,620,746; 3,701,783; 3,733,201; 4,049, 455; 4,095,984; 4,126,459; 4,149,886; 4,150,228; 4,211, 562; 4,248,962; 4,259,437; 4,362,878; 4,409,323; 4,477, 563; 4,782,012; 4,962,018; 4,500,634; 4,579,816; 4,607, 004; 4,618,571; 4,678,739; 4,746,600; 4,746,601; 4,791, 049; 4,857,447; 4,865,959; 4,880,342; 4,886,736; 4,937, 179; 4,946,767; 4,948,716; 4,952,485; 4,956,269; 4,959, 299; 4,966,835; 4,985,336 as well as in patent publications GB 1,560,240; GB 2,007,662; GB 2,032,914; GB 2,099, 167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384, 670; 396,486; 401,612; 401,613. DIR compounds are also disclosed in "Developer-inhibitor-Releasing (DIR) Couplers for Color Photography," C. R. Barr, J. R. Thirtle and P. W. Vittum in Photographic Science and Engineering, Vol. 13, p. 174 (1969), incorporated herein by reference.

It is also contemplated that the present invention may be employed to obtain reflection color prints as described in Research Disclosure, November 1979, Item 18716, available from Kenneth Mason Publications, Ltd., Dudley Annex, 12a North Street, Emsworth, Hampshire P0101 7DQ, England, incorporated herein by reference. The emulsions and materials to form imaging elements may be coated on pH adjusted support as described in U.S. Pat. No. 4,917,994; with epoxy solvents (EP 0 164 961); with additional stabilizers (as described, for example, in U.S. Pat. Nos. 4,346,165; 4,540,653 and 4,906,559); with ballasted chelating agents such as those in U.S. Pat. No. 4,994,359 to reduce sensitivity to polyvalent cations such as calcium; and with stain reducing compounds such as described in U.S. Pat. Nos. 5,068,171 and 5,096,805. Other compounds useful in imaging elements are disclosed in Japanese Published Applications 83-09,959; 83-62,586; 90-072,629, 90-072, 630; 90-072,632; 90-072,633; 90-072,634; 90-077,822; 90-078,229; 90-078,230; 90-079,336; 90-079,338; 90-079, 690; 90-079,691; 90-080,487; 90-080,489; 90-080,490; 90-080,491; 90-080,492; 90-080,494; 90-085,928; 90-086, 669; 90-086,670; 90-087,361; 90-087,362; 90-087,363; 90-087,364; 90-088,096; 90-088,097; 90-093,662; 90-093, 663; 90-093,664; 90-093,665; 90-093,666; 90-093,668; 90-094,055; 90-094,056; 90-101,937; 90-103,409; 90-151, 577.

Silver halide used in photographic imaging elements may be silver iodobromide, silver bromide, silver chloride, silver chlorobromide, silver chloroiodobromide, and the like. For example, in one particular embodiment, the silver halide used in photographic imaging elements of the present invention may contain at least 90 mole % silver chloride or more (for example, at least 95%, 98%, 99% or 100% silver chloride). The type of silver halide grains preferably includes polymorphic, cubic, and octahedral. The grain size of the silver halide may have any distribution known to be useful in photographic compositions, and may be either polydipersed or monodispersed.

Tabular grain silver halide emulsions may also be used. Tabular grains are those with two parallel major faces each clearly larger than any remaining grain face (e.g., ECD/t is at least 2, where ECD is the diameter of a circle having an area equal to grain projected area and t is tabular grain thickness), and tabular grain emulsions are those in which the tabular grains account for at least 50 percent, preferably at least 70 percent and optimally at least 90 percent of total grain projected area. The tabular grains can account for substantially all (e.g., greater than 97 percent) of total grain projected area. The tabular grain emulsions can be high aspect ratio tabular grain emulsions—i.e., ECD/t>8; intermediate aspect ratio tabular grain emulsions—i.e., ECD/t=5 to 8; or low aspect ratio tabular grain emulsions—i.e., ECD/t=2 to 5. The emulsions preferably typically exhibit high tabularity (T), where T (i.e., $ECD/t^2$)>25 and ECD and t are both measured in micrometers ($\mu$m). The tabular grains can be of any thickness compatible with achieving an aim average aspect ratio and/or average tabularity of the tabular grain emulsion. Preferably the tabular grains satisfying projected area requirements are those having thicknesses of <0.3 $\mu$m, thin (<0.2 $\mu$m) tabular grains being specifically preferred and ultrathin (<0.07 $\mu$m) tabular grains being contemplated for maximum tabular grain performance enhancements. When the native blue absorption of iodohalide tabular grains is relied upon for blue speed, thicker tabular grains, typically up to 0.5 $\mu$m in thickness, are contemplated. Tabular grains formed of silver halide(s) that form a face centered cubic (rock salt type) crystal lattice structure can have either {100} or {111} major faces.

Silver halide grains may be prepared according to methods known in the art, such as those described in Research Disclosure I and James, The Theory of the Photographic Process. These include methods such as ammoniacal emulsion making, neutral or acidic emulsion making, and others known in the art. These methods generally involve mixing a water soluble silver salt with a water soluble halide salt in the presence of a protective colloid, and controlling the temperature, pAg, pH values, etc, at suitable values during formation of the silver halide by precipitation.

Silver halide grains may be advantageously subjected to chemical sensitization with noble metal (for example, gold) sensitizers, middle chalcogen (for example, sulfur) sensitizers, reduction sensitizers and others known in the art. Compounds and techniques useful for chemical sensitization of silver halide are known in the art and described in Research Disclosure I and the references cited therein.

Photographic imaging elements provide the silver halide in the form of an emulsion. Photographic emulsions generally include a vehicle for coating the emulsion as a layer of a photographic element. Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), gelatin derivatives (e.g., acetylated gelatin, phthalated gelatin, and the like), and others as described in Research Disclosure I. Also useful as vehicles or vehicle extenders are hydrophilic water-permeable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers, and the like, as described in Research Disclosure I. The vehicle can be present in the emulsion in any amount useful in photographic emulsions. The emulsion can also include any of the addenda known to be useful in photographic emulsions. These include chemical sensitizers, such as active gelatin, sulfur, selenium, tellurium, gold, platinum, palladium, iridium, osmium, rhenium, phosphorous, or combinations thereof. Chemical sensitization is generally carried out at pAg levels of from 5 to 10, pH levels of from 5 to 8, and temperatures of from 30 to 80 C., as described in Research Disclosure I, Section IV (pages 510–511) and the references cited therein.

The silver halide may be sensitized by sensitizing dyes by any method known in the art, such as described in Research Disclosure I. The dye may be added to an emulsion of the silver halide grains and a hydrophilic colloid at any time prior to (e.g., during or after chemical sensitization) or simultaneous with the coating of the emulsion on a photographic element. The dyes may, for example, be added as a solution in water or an alcohol. The dye/silver halide emulsion may be mixed with a dispersion of color image-forming coupler immediately before coating or in advance of coating (for example, 2 hours).

Photographic imaging elements are preferably imagewise exposed using any of the known techniques, including those described in Research Disclosure I, section XVI. This typically involves exposure to light in the visible region of the spectrum, and typically such exposure is of a live image through a lens, although exposure can also be exposure to a stored image (such as a computer stored image) by means of light emitting devices (such as light emitting diodes, CRT and the like).

Photographic imaging elements can be processed in any of a number of well-known photographic processes utilizing any of a number of well-known processing compositions, described, for example, in Research Disclosure I, or in T. H. James, editor, The Theory of the Photographic Process, 4th Edition, Macmillan, N.Y., 1977. In the case of processing a negative working element, the element is treated with a color developer (that is one which will form the colored image dyes with the color couplers), and then with a oxidizer and a solvent to remove silver and silver halide. In the case of processing a reversal color element, the element is first treated with a black and white developer (that is, a developer which does not form colored dyes with the coupler compounds) followed by a treatment to fog silver halide (usually chemical fogging or light fogging), followed by treatment with a color developer. Preferred color developing agents are p-phenylenediamines. Especially preferred are: 4-amino N,N-diethylaniline hydrochloride, 4-amino-3-methyl-N,N-diethylaniline hydrochloride, 4-amino-3-methyl-N-ethyl-N-(b-(methanesulfonamido)ethylaniline sesquisulfate hydrate, 4-amino-3-methyl-N-ethyl-N-(b-hydroxyethyl)aniline sulfate, 4-amino-3-b-(methanesulfonamido)ethyl-N,N-diethylaniline hydrochloride and 4-amino-N-ethyl-N-(2-methoxyethyl)-m-toluidine di-p-toluene sulfonic acid. Development is followed by bleach-fixing, to remove silver or silver halide, washing and drying.

EXAMPLES

The following procedures were used to evaluate hydrophilic colloid coating fluid compositions, as described in the examples set forth below.

Measurement of Gelation Time for Solutions Containing Gelatin and Crosslinker

The tendency of a coating fluid to gel via cross-linking of gelatin molecules by hardener has been correlated with a rise in viscosity ($\eta$) with time (t) after mixing the hardener with the gelatin-containing fluid. The rate of rise of viscosity provides a reliable indicator of the propensity for coating problems caused by "gel slugs". When plotted in the form of fluidity (1/viscosity, $1/\eta(t)$) versus time, there is usually a linear portion to the data, which typically describes the steepest gradient portion of the plot. The linear portion may be extrapolated to a fluidity of zero (i.e. infinite viscosity), and the intersection with the time axis is defined as the "gel time" or gelation time ($t_g$). Use of the steepest gradient portion of the plot thus gives the lowest value of the gel time. The higher the value of the gel time, the less is the propensity to form gel slugs during the manufacturing operation. Thus, a long gel time is desirable. Alternately, it is desired that the product of viscosity and the gelation time ($\eta(t=0) \cdot t_g$) be high, since the gelation time is related to the viscosity of the fluid. The gelation time is calculated from a linear regression, as described by equation 1:

$$\frac{1}{\eta(t)} = \frac{1}{\eta(t=0)} - t\left(\frac{1}{\eta(t=0) \cdot t_g}\right) \qquad \text{Equation 1}$$

Measurements were made with a Bohlin CS50 or a Bohlin CVO120 controlled-stress rheometer. The sample was contained in a Bohlin C2.3/26 geometry and measurements of viscosity were made typically at 30 s intervals at a constant applied stress of 0.4 Pa. The fitting region of the fluidity-time plot was always that with the steepest slope, which gives the lowest value for the predicted gelation time. The time of mixing of gelatin-containing fluid (or "melt") with the hardener solution was taken to be the start time of the reaction. Viscosity measurements commenced a few minutes after mixing of the melt with the hardener solution.

In the examples, the gelation times of gelatin solutions and more complex coating fluids were compared for conventionally-manufactured lime-hydrolysed ossein gelatin and solubilized collagen gelatin that had been manufactured by a strong-alkali process as described in U.S. Pat. No. 5,908,921. As part of this novel process, the solubilized collagen gelatins were deionised with mix-bed ion-exchange resins and adjusted from the iso-electric pH at 4.9 to pH 5.65–5.85 with NaOH or KOH. Some of the gelatins made by the conventional process had undergone this de-ionisation procedure and these are referred to as "DI" gelatins. The conventional gelatins referred to as "non DI" had not been deionised, and so contained divalent cations, but had been adjusted to the same pH range of 5.65–5.85. The gelatins contain approximately 11% moisture, which has not been accounted for in the concentrations quoted. The hardener used was either one of two solutions of BVSM (bis(vinylsulphonyl)methane): HARDENER-1, which contains 1.8% w/w BVSM and 19.5 mM $KNO_3$; or HARDENER-2, which contains 2.1% w/w BVSM and 0.01% w/w citric acid.

Solution viscosity is an important factor influencing the gelation time. The viscosity is controlled primarily by the gelatin concentration and the gelatin mean molecular weight. The mean molecular weight can be difficult to determine precisely. Here, the viscosity of a 20% w/w gelatin solution at 45° C. ($\eta 20\%$) is used to characterise the mean molecular weight. The gelatins may also be characterised by the gel strength or bloom. The gel strength is measured for a 6.16% dry weight gelatin after 24 hours hold at 10.0° C. It is the weight in grams required to depress a plunger (of 0.5" diameter, with a $1/64^{th}$" radius of curvature at the bottom) by 4 mm.

Example 1

Solutions of Gelatin and Hardener at Constant Initial Viscosity and Hardener Concentration Three sets of gelatin and hardener solutions were prepared for evaluating gelation times. One set (Samples 1.1–1.13) was prepared with solubilized collagen gelatins of varying mean molecular weight (as indicated by $\eta 20\%$) obtained using the process described in U.S. Pat. No. 5,908,921. A second set (Samples 1.14–1.26) was prepared with conventional deionized gelatins obtained from lime hydrolyzed ossein. A third set (Samples 1.27–1.36) was prepared with conventional non-deionized gelatins obtained from lime hydrolyzed ossein. Gelation time was determined for gelatin solutions with HARDENER-1 at 40.0° C. The concentration of HARDENER-1 in all the samples was 30% w/w (27.6 micromoles hardener per gram of solution), and the gelatin concentrations were from about 6 to 13 eight %, with the concentrations set for each sample such that the initial solution viscosities were generally between 11 and 13 mpa·s at 40.0° C. (the concentration of gelatin thus decreased with increasing molecular weight, or $\eta 20\%$). The extrapolated initial viscosity, the gelation time, and their product for each sample are given in Table 1.

TABLE 1

Gelation time $t_g$ of gelatin solutions of different MW (as indicated by $\eta 20\%$) at concentrations to give the same initial viscosity ($\eta(t = 0)$).

| Sample | $\eta 20\%$ (mPa · s) | $\eta(t = 0)$ (mPa · s) | $t_g$ (min) | $\eta(t = 0) \cdot t_g$ (Pa · s · min) |
|---|---|---|---|---|
| Solubilized collagen gelatins | | | | |
| 1.1 | 37 | 12.1 | 111 | 1.34 |
| 1.2 | 39 | 12.3 | 118 | 1.45 |
| 1.3 | 62 | 11.8 | 105 | 1.23 |
| 1.4 | 66 | 12.3 | 109 | 1.33 |
| 1.5 | 68 | 11.3 | 113 | 1.28 |
| 1.6 | 71 | 11.5 | 107 | 1.23 |
| 1.7 | 80 | 12.0 | 100 | 1.20 |
| 1.8 | 94 | 12.8 | 91 | 1.16 |
| 1.9 | 94 | 13.0 | 91 | 1.18 |
| 1.10 | 140 | 12.2 | 90 | 1.10 |
| 1.11 | 146 | 11.8 | 94 | 1.11 |
| 1.12 | 152 | 12.3 | 88 | 1.08 |
| 1.13 | 177 | 12.6 | 82 | 1.04 |
| Conventional DI gelatins | | | | |
| 1.14 | 54 | 12.4 | 93 | 1.16 |
| 1.15 | 65 | 12.1 | 90 | 1.08 |
| 1.16 | 73 | 12.0 | 85 | 1.02 |
| 1.17 | 100 | 12.5 | 76 | 0.95 |
| 1.18 | 111 | 11.4 | 81 | 0.92 |
| 1.19 | 136 | 12.3 | 73 | 0.90 |
| 1.20 | 147 | 11.4 | 81 | 0.92 |
| 1.21 | 159 | 12.1 | 64 | 0.78 |
| 1.22 | 161 | 11.9 | 70 | 0.84 |
| 1.23 | 162 | 11.9 | 68 | 0.80 |
| 1.24 | 189 | 11.0 | 68 | 0.74 |
| 1.25 | 280 | 13.3 | 61 | 0.81 |
| 1.26 | 412 | 12.9 | 56 | 0.72 |
| Conventional non-DI gelatins | | | | |
| 1.27 | 39 | 11.2 | 106 | 1.19 |
| 1.28 | 42 | 11.5 | 93 | 1.07 |
| 1.29 | 59 | 11.0 | 91 | 1.00 |
| 1.30 | 67 | 10.4 | 97 | 1.01 |
| 1.31 | 117 | 10.5 | 84 | 0.88 |
| 1.32 | 174 | 11.5 | 66 | 0.76 |
| 1.33 | 184 | 11.6 | 67 | 0.78 |
| 1.34 | 195 | 11.5 | 63 | 0.72 |
| 1.35 | 200 | 10.6 | 72 | 0.76 |
| 1.36 | 230 | 10.2 | 70 | 0.71 |

The above data illustrate that gelation times (and the product $\eta(t=0) \cdot t_g$) decrease as the mean MW ($\eta 20\%$) of the gelatin increases. Over the whole range of MW studied, the gelation times are approximately 20% greater for solubilized collagen gelatins than for conventional gelatins of the same MW, independent of whether the conventional gelatins had been deionized.

Example 2
Solutions of Gelatin and Hardener at Constant Hardener-to-gelatin Ratio The chemical gelation of a conventional DI lime-processed gelatin and a solubilized collagen gelatin with the same $\eta 20\%$ (157 mPa·s) were compared at a constant ratio of gelatin to hardener. Solutions of 20% w/w gelatin were mixed with HARDENER-1 at a volume ratio of 4:3 to obtain a gelatin:BVSM weight ratio of 8:0.54 (340 micromoles of BVSM per gram of gelatin), and diluted with water to provide solutions of varying concentrations (solubilized collagen gelatin solution samples 2.1–2.3, and conventional lime processed gelatin samples 2.4–2.6). Gelation times were determined for the gelatin solutions at 40.0° C. The extrapolated initial viscosity, the gelation time, and their product for each sample are given in Table 2.

TABLE 2

Chemical gelation times and initial viscosity for gelatin solutions with BVSM.

| Sample | Gelatin Concentration (% w/w) | $\eta\eta(t = 0)$ (mPa · s) | $t_g$ (min) | $\eta(t = 0) \cdot t_g$ (Pa · s · min) |
|---|---|---|---|---|
| Solubilized collagen gelatin | | | | |
| 2.1 | 10 | 19.9 | 52 | 1.042 |
| 2.2 | 8 | 12.6 | 83 | 1.045 |
| 2.3 | 6 | 7.7 | 160 | 1.223 |
| Conventional gelatin | | | | |
| 2.4 | 10 | 17.3 | 48 | 0.824 |
| 2.5 | 8 | 11.5 | 71 | 0.819 |
| 2.6 | 6 | 8.3 | 123 | 1.015 |

The above data illustrate the gelation times were advantageously found to be longer for the solubilized collagen gelatin solutions than for the conventional gelatin solutions. The product of gelation time and extrapolated initial viscosity was 20–30% higher for the solubilized collagen gelatin samples.

Example 3
Solutions of Gelatin, Polyanion Thickener and Hardener

The chemical gelation times of conventional DI lime-processed gelatin and solubilized collagen gelatin solutions to which a water-soluble polymeric thickener (co-polymer of acrylamide (20% w/w) and sodium 2-acrylamido-2-methylpropane sulfonate (80% w/w)) was added to increase the viscosity were compared at varying gelatin and thickener concentrations. The concentration of HARDENER-1 in each coating fluid was 30% w/w (the BVSM concentration was 27.5 micromoles per gram of solution). Two solubilized collagen gelatin samples were compared with a conventional DI gelatin sample. Solubilized collagen 1 ($\eta 20\%=177$ mPa·s, gel strength 331 g) used in Samples 3.1–3.10 had a slightly higher solution viscosity than solubilized collagen 2 ($\eta 20\%=159$ mPa·s, gel strength 335 g) used in Samples 3.11–3.21 and the conventional DI gelatin ($\eta 20\%=157$ mPa·s, gel strength 281 g) used in samples 3.22–3.33. Gelation times were determined for the gelatin solutions at 40.0° C. The extrapolated initial viscosity, the gelation time, and their product for each sample are given in Table 3.

TABLE 3

Gelation time of solutions of conventional gelatins and solubilized collagen gelatins in the presence of a polyanionic thickener.

| Sample | Thickener (% w/w) | Gelatin (% w/w) | Thickener/Gelatin (% w/w) | $\eta(t = 0)$ (mPa · s) | $t_g$ (min) | $\eta(t = 0) \cdot t_g$ (Pa · s · min) |
|---|---|---|---|---|---|---|
| Solubilized collagen gelatin 1 | | | | | | |
| 3.1 | 0 | 8 | 0.00 | 15 | 70 | 1.03 |
| 3.2 | 0.1 | 8 | 1.25 | 36 | 61 | 2.18 |

TABLE 3-continued

Gelation time of solutions of conventional gelatins and solubilized collagen gelatins in the presence of a polyanionic thickener.

| Sample | Thickener (% w/w) | Gelatin (% w/w) | Thickener/Gelatin (% w/w) | η(t = 0) (mPa · s) | $t_g$ (min) | η(t = 0) · $t_g$ (Pa · s · min) |
|---|---|---|---|---|---|---|
| 3.3 | 0.3 | 8 | 3.75 | 82 | 61 | 5.02 |
| 3.4 | 0.5 | 8 | 6.25 | 114 | 70 | 7.99 |
| 3.5 | 0 | 6 | 0.00 | 9 | 110 | 0.99 |
| 3.6 | 0.1 | 6 | 1.67 | 24 | 81 | 1.95 |
| 3.7 | 0.3 | 6 | 5.00 | 58 | 83 | 4.82 |
| 3.8 | 0.5 | 6 | 8.33 | 80 | 100 | 7.95 |
| 3.9 | 0.1 | 4 | 2.50 | 17 | 127 | 2.10 |
| 3.10 | 0.3 | 4 | 7.50 | 39 | 130 | 5.09 |
| Solubilized collagen gelatin 2 | | | | | | |
| 3.11 | 0 | 8 | 0.00 | 12 | 88 | 1.06 |
| 3.12 | 0.1 | 8 | 1.25 | 31 | 68 | 2.08 |
| 3.13 | 0.3 | 8 | 3.75 | 66 | 73 | 4.83 |
| 3.14 | 0.5 | 8 | 6.25 | 94 | 79 | 7.48 |
| 3.15 | 0 | 6 | 0.00 | 7 | 143 | 1.06 |
| 3.16 | 0.1 | 6 | 1.67 | 21 | 92 | 1.93 |
| 3.17 | 0.3 | 6 | 5.00 | 47 | 96 | 4.46 |
| 3.18 | 0.5 | 6 | 8.33 | 65 | 112 | 7.33 |
| 3.19 | 0.1 | 4 | 2.50 | 14 | 159 | 2.18 |
| 3.20 | 0.3 | 4 | 7.50 | 31 | 154 | 4.72 |
| 3.21 | 0.5 | 4 | 12.50 | 43 | 187 | 8.01 |
| Conventional DI gelatin | | | | | | |
| 3.22 | 0 | 8 | 0.00 | 12 | 67 | 0.80 |
| 3.23 | 0.1 | 8 | 1.25 | 34 | 50 | 1.67 |
| 3.24 | 0.3 | 8 | 3.75 | 77 | 55 | 4.19 |
| 3.25 | 0.5 | 8 | 6.25 | 107 | 62 | 6.64 |
| 3.26 | 0.5 | 8 | 6.25 | 106 | 62 | 6.55 |
| 3.27 | 0 | 6 | 0.00 | 7 | 112 | 0.82 |
| 3.28 | 0.1 | 6 | 1.67 | 24 | 66 | 1.57 |
| 3.29 | 0.3 | 6 | 5.00 | 54 | 75 | 4.08 |
| 3.30 | 0.5 | 6 | 8.33 | 75 | 90 | 6.73 |
| 3.31 | 0.1 | 4 | 2.50 | 16 | 109 | 1.70 |
| 3.32 | 0.3 | 4 | 7.50 | 38 | 117 | 4.44 |
| 3.33 | 0.5 | 4 | 12.50 | 51 | 146 | 7.44 |

For the same gelatin and thickener concentrations, the product of gelation time and initial viscosity is approximately 20% higher for the solutions containing solubilized collagen gelatin relative to solutions containing the conventional DI gelatin.

Example 4
Chemical Gelation in Coating Fluid Containing Dispersed Hydrophobic Material Phase Particles The gelation time of aqueous gelatin coating fluids containing an oil-in-water dispersion of a photographically useful material was determined. The coating fluid was obtained by first preparing a parent dispersion by dissolving scavenger DMBHQ (2,5-di-(1,1,3,3-tetramethylbutyl) hydroquinone) in solvent CS-2 (weight ratio of 1:1.829) and heating to 110° C. This oil phase is then added to an aqueous gelatin solution containing deionized lime-processed bone gelatin and surfactant Alkanol-XC™ (Dupont), held at 80° C. The resulting mixture is subjected to a Brinkmann rotor-stator mixer, set at 8000 rpm for 2 minutes, and then homogenized by passing once through a multiple orifice device at 352 kg/cm², at a temperature of 80° C. The resulting dispersion has a concentration of DMBHQ of 8.08% w/w, 14.8% w/w organic solvent CS-2, 8.56% w/w gelatin, and 0.625% Alkanol-XC™, and had a particle size of 0.35 microns.

The parent dispersion was diluted with a 20% w/w gelatin solution and additional water, where the gelatin solution used for dilution comprised either a solubilized collagen gelatin (η20% =112 mPa·s) in Sample 4.1, or a conventional lime processed DI gelatin having an identical η20% viscosity in Sample 4.2. To match the level of ions in the solubilized collagen gelatin sample, potassium (in the form of potassium sulfate) was added to the conventional DI gelatin at 3480 ppm, as the solubilized collagen gelatin sample contained a higher level of ions than the conventional DI gelatin. The gelatin solution used for dilution supplied 84.9% w/w of the total gelatin in the diluted dispersion. Composition of the diluted dispersions was as indicated in Table 4a.

TABLE 4a

Composition of diluted dispersions.

| Composition | Mass in 100 g (g) | Gelatin in parent dispersion (% w/w) | Gelatin (% w/w) | Gelatin added in diluted dispersion (% w/w) | Dispersed Organic phase (% w/w) |
|---|---|---|---|---|---|
| Total | 100 | | 16.132 | 84.9% | 6.52 |
| Parent dispersion | 28.53 | 8.56 | 2.44 | | |
| 20% gelatin solution | 68.46 | | 13.692 | | |
| Water | 3.01 | | | | |

The resulting diluted dispersions were then mixed with a polymeric thickener solution and a hardener solution to form a coating fluid (8.588 g diluted dispersion, 1.092 g of thickener solution and 10.30 g of HARDENER-2), and the gelation time was then measured. The hardener HARDENER-2 contains 2.1% w/w BVSM and 0.01% w/w citric acid. The thickener solution contains 8% w/w of a water-soluble co-polymer of acrylamide (20% w/w) and sodium 2-acrylamido-2-methylpropane sulfonate (80% w/w). The coating fluid contained a total of 6.93% w/w gelatin, of which 1.03% w/w was conventional DI gelatin from the parent dispersion, and 5.90% w/w gelatin was either conventional DI gelatin or solubilized collagen gelatin. There was 2.80% w/w colloidally-dispersed organic material. The BVSM hardener was present at 55 micromoles per gram of coating fluid (796 micromoles per gram of gelatin). An additional coating fluid, Sample 4.3, was prepared similarly as in sample 4.2 with the addition of conventional gelatin to the parent dispersion, with the diluted dispersion further diluted with water by an additional 2% in order to reduce the initial viscosity. The viscosity rise with time was measured at 45° C. and the gelation time values are given in Table 4b.

TABLE 4b

Gelation time of dispersion coating fluid with HARDENER-2 at 45° C.

| Sample | Added gelatin | η(t = 0) (mPa · s) | $t_g$ (min) | η(t = 0) · $t_g$ (Pa · s · min) |
|---|---|---|---|---|
| 4.1 | Solubilized collagen | 72.9 | 58.3 | 4.25 |
| 4.2 | Conventional DI + $K_2SO_4$ | 73.5 | 52.1 | 3.83 |
| 4.3 | Conventional DI + $K_2SO_4$ + 2% dilution | 67.7 | 51.7 | 3.51 |

The above data illustrates that gelation times were longer for the solubilized collagen-gelatin containing coating fluids. The coating fluid containing conventional lime processed gelatin had a 10% lower value of the product of gelation time and initial viscosity than the same concentration solubilized collagen-gelatin containing fluid. The coating fluid with conventional gelatin diluted by 2% with water in order to reduce the initial viscosity had a 20% lower value of the product η(t=0)·$t_g$. Thus in aqueous coating fluids containing dispersed particles, polymeric thickeners, and gelatin hardener it is advantageous to use a solubilized collagen gelatin in order to minimize manufacturing problems related to gelatin slugs.

Example 5

A color-negative imaging element on reflective support is prepared by coating aqueous coating solutions of the following layers on a resin-coated paper support. In the coating structure, a blue imaging layer comprising a yellow coupler mixed with a blue-sensitive chloro-iodide cubic emulsion (0.2 mole % iodide, 0.6 μm cubic edge length average grain size) is the first layer of a three-color photographic recording material on the support. The subsequent layers comprise, in order, a layer containing a scavenger for oxidized developer, a green imaging layer, a second scavenger layer, a red imaging layer, a uv absorbing layer and a protective gelatin super-coat. The green imaging layer comprises a dispersion of magenta coupler mixed with a green-sensitive chloride cubic emulsion (0.3 μm cubic edge length average grain size) while red-sensitized chloride emulsion (0.4 μm cubic edge length average grain size) is mixed with a dispersion of cyan couplers to form the red imaging layer. Details of the structure of the multilayer coating, including component coverages in each layer, are shown below.

Layer 4 (Interlayer B) is coated from an aqueous coating fluid in accordance with the invention comprising gelatin at a concentration of 6.93 wt % and gelatin hardener at a level of 55 μmole hardener (BVSM) per gram of coating fluid, with 84.9 wt % of the gelatin in the coating fluid comprising a solubilized collagen gelatin prepared from hydrolysis of ossein using sodium or potassium hydroxide, having an η20%=112 mPa·s. The coating fluid is prepared as described in Example 4. Decreased generation of gel slug formation in the Layer 4 coating fluid is observed due to use of solubilized collagen gelatin. Further benefit may be obtained in the use of such gelatin in the preparation of the parent oil-in-water dispersion of photographically useful material contained in the coating fluid.

| Coating structure | |
|---|---|
| Layer 7 (Supercoat) | |
| Ludox AM ® (Dupont) | 0.1614 g · m$^{-2}$ |
| Gelatin (acid-processed) | 0.6456 g · m$^{-2}$ |
| Layer 6 (UV Layer) | |
| Tinuvin-328 ® | 0.130 g · m$^{-2}$ |
| Tinuvin 326 ® | 0.023 g · m$^{-2}$ |
| DMBHQ | 0.042 g · m$^{-2}$ |
| CS-3 | 0.051 g · m$^{-2}$ |
| Gelatin | 0.525 g · m$^{-2}$ |
| Layer 5 (Red-sensitive Layer) | |
| Ag | 0.198 g · m$^{-2}$ |
| Coupler CC-1 | 0.232 g · m$^{-2}$ |
| Coupler CC-2 | 0.026 g · m$^{-2}$ |

| Coating structure | |
|---|---|
| Tinuvin 328 ® | 0.355 g · m$^{-2}$ |
| CS-3 | 0.145 g · m$^{-2}$ |
| CS-4 | 0.436 g · m$^{-2}$ |
| Gelatin | 1.312 g · m$^{-2}$ |
| Layer 4 (Interlayer B) | |
| DMBHQ | 0.108 g · m$^{-2}$ |
| CS-2 | 0.197 g · m$^{-2}$ |
| Gelatin | 0.753 g · m$^{-2}$ |
| Hardener | 0.1175 g · m$^{-2}$ |
| Polymeric thickener | 0.046 g · m$^{-2}$ |
| Layer 3 (Green-sensitive Layer) | |
| Ag | 0.099 g · m$^{-2}$ |
| Coupler MC-1 | 0.208 g · m$^{-2}$ |
| St-4 | 0.040 g · m$^{-2}$ |
| St-3 | 0.274 g · m$^{-2}$ |
| CS-5 | 0.218 g · m$^{-2}$ |
| CS-2 | 0.112 g · m$^{-2}$ |
| Gelatin | 1.187 g · m$^{-2}$ |
| Layer 2 (Interlayer A) | |
| DMBHQ | 0.108 g · m$^{-2}$ |
| CS-2 | 0.197 g · m$^{-2}$ |
| Gelatin | 0.753 g · m$^{-2}$ |
| Layer 1 (Blue-sensitive Layer) | |
| Ag | 0.217 g · m$^{-2}$ |
| Coupler YC-1 | 0.414 g · m$^{-2}$ |
| St-1 | 0.173 g · m$^{-2}$ |
| St-2 | 0.025 g · m$^{-2}$ |
| St-4 | 0.099 g · m$^{-2}$ |
| CS-1 | 0.218 g · m$^{-2}$ |
| HQ-K | 0.0095 g · m$^{-2}$ |
| PHR | 0.0011 g · m$^{-2}$ |
| Gelatin | 1.244 g · m$^{-2}$ |

Support

PHR = 2,5-dihydroxy-5-methyl-3-(1-piperidenyl)-2-cyclopenten-1-one

HQ-K = 2,5-dihydroxy-4-(1-methylheptadecyl)-benzenesulphonic acid (K salt)

DMBHQ = 2,5-(di-(1,1,3,3-tetramethylbutyl)hydroquinone

Hardener = bis(vinylsulphonyl)methane (BVSM)

Polymeric thickener = co-polymer of acrylamide (20% w/w) and sodium 2-acrylamido-2-methylpropane sulfonate (80% w/w)

Stabilizer St-1

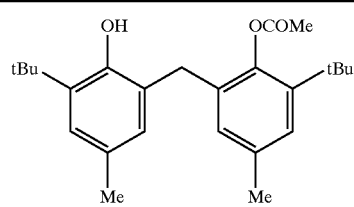

-continued
Stabilizer St-2
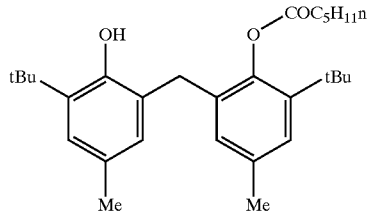
Stabilizer St-3
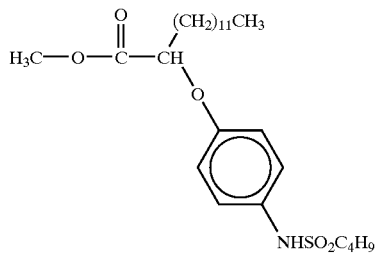
Stabilizer St-4
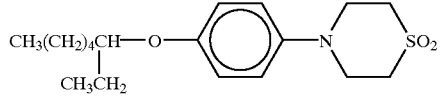
Solvent CS-1
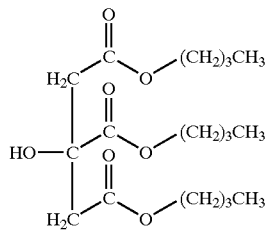
Solvent CS-2
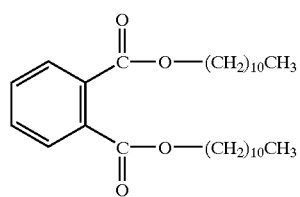
Solvent CS-3
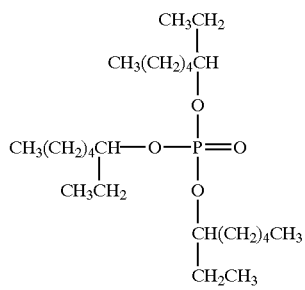
Solvent CS-4
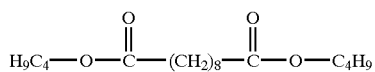
Solvent CS-5    $CH_3(CH_2)_7CH=CH(CH_2)_8—OH$ -continued Coupler YC-1
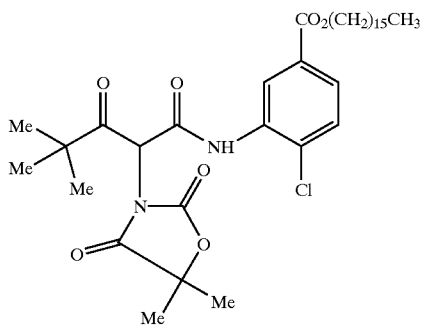

Coupler MC-1
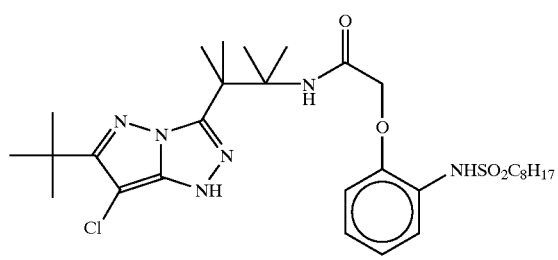

Coupler CC-1
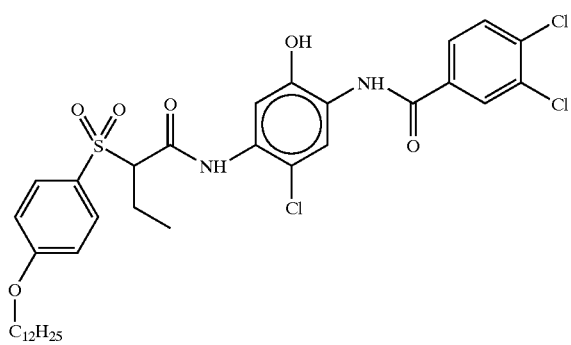

Coupler CC-2
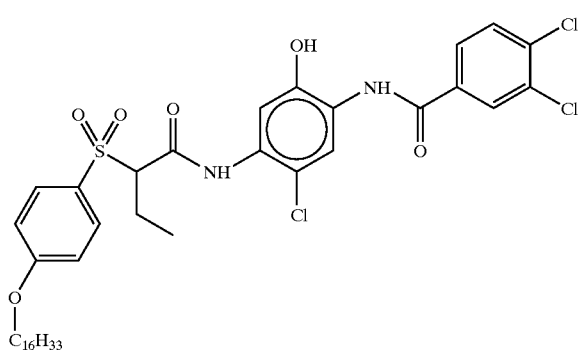

Example 6

A color-negative imaging element on reflective support is prepared similarly as in Example 5, except (i) the Hardener and the Polymeric thickener are not present in the coating fluid for Layer 4, and (ii) coating Layer 1 additionally contains Hardener (BVSM) coated at 0.125 g/m², and thickener poly(sodium 2-acrylamido-2-methylpropane sulfonate) coated at 0.024 g/m². The Layer 1 is coated from an aqueous coating fluid in accordance with the invention comprising gelatin at a concentration of approximately 3 wt % and gelatin hardener at a level of approximately 16 μmole hardener per gram of coating fluid, with 80 wt % of the gelatin in the coating fluid comprising a solubilized collagen gelatin prepared from hydrolysis of ossein using sodium or potassium hydroxide, having an η20%=112 mPa·s. Decreased generation of gel slug formation in the Layer 1 coating fluid is observed due to use of solubilized collagen gelatin.

The invention has been described in detail with particular reference to certain preferred embodiments thereof, but it will be understood that variations and modifications can be effected within the spirit and scope of the invention.

What is claimed is:

1. An aqueous coating fluid comprising gelatin at a concentration of at least 1 wt % and gelatin hardener at a level from 1–200 effective μmole hardener per gram of coating fluid, wherein at least 20% of the gelatin comprises a gelatin prepared from hydrolysis of ossein using sodium or potassium hydroxide.

2. A coating fluid according to claim 1, wherein the hardener level is from 10–100 effective μmole hardener per gram of coating fluid.

3. A coating fluid according to claim 1, wherein the hardener level is from 10–70 effective μmole hardener per gram of coating fluid.

4. A coating fluid according to claim 1, wherein the hardener level is from 20–60 effective μmole hardener per gram of coating fluid.

5. A coating fluid according to claim 1, wherein at least 30% of the gelatin comprises a gelatin prepared from hydrolysis of ossein using sodium or potassium hydroxide.

6. A coating fluid according to claim 1, wherein at least 50% of the gelatin comprises a gelatin prepared from hydrolysis of ossein using sodium or potassium hydroxide.

7. A coating fluid according to claim 1, wherein the hardener is a vinyl sulfone hardener.

8. A coating fluid according to claim 7, wherein the vinyl sulfone hardener is bis(vinyl-sulfonyl) methane, bis(vinyl-sulfonyl methyl) ether, or 1,2-bis(vinyl-sulfonyl acetoamide)ethane.

9. A coating fluid according to claim 7, wherein the vinyl sulfone hardener is a polymeric vinyl sulfone.

10. A coating fluid according to claim 1, wherein the gelatin prepared from hydrolysis of ossein using sodium or potassium hydroxide is prepared by a process comprising:
  providing a collagen containing material;
  demineralizing the collagen containing material to produce ossein;
  adding the ossein to a water solution containing at least 4% sodium hydroxide or potassium hydroxide and at least 3% sodium sulfate for a time sufficient to form a reacted slurry;
  heating the slurry to at least 45 C. for a time sufficient to produce a solution containing gelatin;
  raising the pH of the gelatin solution to greater than 9.8;
  adding a sulfate salt of a divalent or trivalent cation to the gelatin solution to reduce the pH to between 7.0 and 8.0;
  adding an acid to the gelatin solution to reduce the pH to between 5.0 and 6.0;
  adding a polymeric flocculant to the gelatin solution in an amount of about 0.1 percent based on a dry weight of the gelatin to produce a floc;
  removing the floc from the gelatin solution;
  filtering the gelatin solution; and
  desalting the gelatin solution.

11. A coating fluid according to claim 1, comprising gelatin at a concentration of at least 3 wt %.

12. A coating fluid according to claim 1, comprising gelatin at a concentration of at least 4 wt %.

13. A coating fluid according to claim 1, comprising gelatin at a concentration of at least 5 wt %.

14. A coating fluid according to claim 1, wherein the low-shear viscosity of the fluid is above 3 mPa·s when measured at 45° C.

15. A coating fluid according to claim 1, wherein the low-shear viscosity of the fluid is above 5 mPa·s when measured at 45° C.

16. A coating fluid according to claim 1, wherein the MW of the elatin in the coating fluid, as defined by the solution viscosity η20%, is greater than 30 mPa·s.

17. A coating fluid according to claim 1, wherein the MW of the gelatin in the coating fluid, as defined by the solution viscosity η20%, is greater than 40 mPa·s.

18. A coating fluid according to claim 1, further comprising an anionic polymeric thickener at a concentration above 0.01% wt %.

19. A coating fluid according to claim 1, further comprising dispersed hydrophobic material phase particles.

20. A coating fluid according to claim 1, wherein the hardener is present at a level greater than 100 effective μmole hardener per gram of gelatin in solution.

21. A coating fluid according to claim 1, wherein the hardener is present at a level greater than 300 effective μmole hardener per gram of gelatin in solution.

22. A coating fluid according to claim 1, wherein the hardener is present at a level greater than 500 effective μmole hardener per gram of gelatin in solution.

* * * * *